(12) United States Patent
Blaschke et al.

(10) Patent No.: US 9,809,526 B2
(45) Date of Patent: Nov. 7, 2017

(54) METHOD FOR THE CONTINUOUS DEHYDRATION OF 3-HYDROXYPROPIONIC ACID TO FORM ACRYLIC ACID

(71) Applicant: BASF SE, Ludwigshafen (DE)

(72) Inventors: Tim Blaschke, Ekeren (BE); Ortmund Lang, Quirnbach (DE); Marta Zajaczkowski-Fischer, Neuhofen (DE); Marco Hartmann, Jockgrim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/311,541

(22) PCT Filed: May 13, 2015

(86) PCT No.: PCT/EP2015/060639
§ 371 (c)(1),
(2) Date: Nov. 16, 2016

(87) PCT Pub. No.: WO2015/177029
PCT Pub. Date: Nov. 26, 2015

(65) Prior Publication Data
US 2017/0081268 A1    Mar. 23, 2017

(30) Foreign Application Priority Data
May 19, 2014  (EP) .................... 14168770

(51) Int. Cl.
C07C 51/46   (2006.01)
C07C 51/377  (2006.01)
C07C 51/43   (2006.01)

(52) U.S. Cl.
CPC ............ *C07C 51/46* (2013.01); *C07C 51/377* (2013.01); *C07C 51/43* (2013.01)

(58) Field of Classification Search
CPC .................................................. C07C 51/377
See application file for complete search history.

(56) References Cited

U.S. PATENT DOCUMENTS

| | | | |
|---|---|---|---|
| 5,504,247 A | 4/1996 | Saxer et al. | |
| 8,198,481 B2 | 6/2012 | Kuppinger et al. | |
| 8,293,941 B2 | 10/2012 | Kuppinger et al. | |
| 8,481,784 B2 | 7/2013 | Kuppinger et al. | |
| 8,895,683 B2 | 11/2014 | Kuppinger et al. | |
| 9,309,180 B2 * | 4/2016 | Kuppinger | C07C 51/377 |
| 2007/0219390 A1 | 9/2007 | Zacher et al. | |
| 2014/0018574 A1 | 1/2014 | Raith et al. | |

FOREIGN PATENT DOCUMENTS

| | | |
|---|---|---|
| DE | 102012212424 A1 | 1/2014 |
| EP | 0616998 A1 | 9/1994 |
| EP | 2565211 A1 | 3/2013 |
| WO | WO-2007/106100 A1 | 9/2007 |
| WO | WO-2008/023039 A1 | 2/2008 |
| WO | WO-2014/111363 A1 | 7/2014 |
| WO | WO-2015/036218 A1 | 3/2015 |
| WO | WO-2015/036273 A1 | 3/2015 |
| WO | WO-2015/036278 A1 | 3/2015 |
| WO | WO-2015/177026 A1 | 11/2015 |

OTHER PUBLICATIONS

International Search Report (English translation), International Application No. PCT/EP2015/060639, dated Jul. 3, 2015.

* cited by examiner

*Primary Examiner* — Paul A Zucker
(74) *Attorney, Agent, or Firm* — Marshall, Gerstein & Borun LLP

(57) ABSTRACT

The invention relates to a process for dehydrating aqueous 3-hydroxypropionic acid to acrylic acid, wherein an aqueous mixture of 3-hydroxypropionic acid and oligomeric 3-hydroxypropionic acid is converted to acrylic acid in the liquid phase in a first step and aqueous acrylic acid is distilled out of the liquid phase, and the aqueous acrylic acid is separated by distillation into an acrylic acid-rich phase and a water-rich phase in a second step.

12 Claims, No Drawings

METHOD FOR THE CONTINUOUS DEHYDRATION OF 3-HYDROXYPROPIONIC ACID TO FORM ACRYLIC ACID

CROSS-REFERENCE TO RELATED APPLICATIONS

This is the U.S. National Phase of International Application No. PCT/EP2015/060639, filed May 13, 2015, which claims the benefit of European Patent Application No. 14168770.7, filed May 19, 2014.

The invention relates to a process for dehydrating aqueous 3-hydroxypropionic acid to acrylic acid, wherein an aqueous mixture of 3-hydroxypropionic acid and oligomeric 3-hydroxypropionic acid is converted to acrylic acid in the liquid phase and aqueous acrylic acid is distilled out of the liquid phase and the aqueous acrylic acid is separated by distillation into an acrylic acid-rich phase and a water-rich phase in a second step.

Because of its very reactive double bond and its carboxylic acid group, acrylic acid is a valuable monomer for preparation of polymers, for example water-absorbing polymer particles, binders for water-based emulsion paints, and adhesives dispersed in aqueous solvent.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

On the industrial scale, acrylic acid is prepared almost exclusively from fossil raw materials. This is regarded as disadvantageous by the consumers of the hygiene articles. There is therefore a need to produce the water-absorbing polymer particles used in the hygiene articles from renewable raw materials.

One possible route is the fermentative preparation of 3-hydroxypropionic acid and the conversion thereof to acrylic acid. The preparation of 3-hydroxypropionic acid by fermentation is described, for example, in WO 2012/074818 A2.

The dehydration of 3-hydroxypropionic acid in the gas phase is mentioned in U.S. Pat. No. 7,538,247.

The dehydration of 3-hydroxypropionic acid in the liquid phase is mentioned, for example, in WO 2006/092271 A2, WO 2008/023039 A1, JP 2010-180171, EP 2 565 211 A1 and EP 2 565 212 A1.

It was an object of the present invention to provide an improved process for preparing acrylic acid based on renewable raw materials.

The object was achieved by a process for continuously dehydrating aqueous 3-hydroxypropionic acid to acrylic acid, which comprises, in a first step i), converting an aqueous mixture of 3-hydroxypropionic acid and oligomeric 3-hydroxypropionic acid to acrylic acid in the liquid phase and at a pressure of less than 900 mbar and separating aqueous acrylic acid from the liquid phase by distillation and, in a second step ii), separating the aqueous acrylic acid obtained in step i) at a pressure of less than 900 mbar by distillation into an acrylic acid-rich phase and a water-rich phase.

The pressure is the pressure in the reactor or, in the case of a distillation, the pressure in the bottom of the still.

The aqueous mixture of monomeric 3-hydroxypropionic acid and oligomeric 3-hydroxypropionic acid used in step i) comprises preferably from 5 to 50% by weight of water, more preferably from 10 to 40% by weight of water, most preferably from 15 to 35% by weight of water.

The aqueous mixture of monomeric 3-hydroxypropionic acid and oligomeric 3-hydroxypropionic acid used in step i) comprises preferably from 10 to 60% by weight of monomeric 3-hydroxypropionic acid, more preferably from 20 to 50% by weight of monomeric 3-hydroxypropionic acid, most preferably from 25 to 45% by weight of monomeric 3-hydroxypropionic acid.

The present invention is based on the finding that the concentration of acrylic acid in the liquid phase can be kept low under reduced pressure. This reduces the risk of unwanted free-radical polymerization in step i). Furthermore, the distillative separation in step ii) under reduced pressure and at the associated lower temperatures gives rise to less oligomeric acrylic acid.

The liquid phase in step i) advantageously comprises a high-boiling organic solvent. The high-boiling organic solvent dilutes the acrylic acid and high-boiling by-products (high boilers) formed in the liquid phase.

The aqueous acrylic acid formed in the reaction in step i) is removed by distillation. Rectification columns are particularly suitable for this purpose (rectification column 2). Through the selection of the separation plates and of the reflux ratio, the content of 3-hydroxypropionic acid in the distillate can be kept low.

The aqueous acrylic acid obtained in step i) is separated by distillation into an acrylic acid-rich phase (crude acrylic acid) and a water-rich phase (acid water). The separation can be facilitated using an entraining agent. Suitable entraining agents are low-boiling hydrophobic organic solvents. Rectification columns are likewise particularly suitable for the distillative separation (rectification column 3).

Particularly advantageously, the rectification column 2 and the rectification column 3 are combined to a single rectification column 4. In this case, the removal of the aqueous acrylic acid from the liquid phase in step i) and/or separation of the aqueous acrylic acid into an acrylic acid-rich phase and a water-rich phase in step ii) is performed in the rectification column 4, with removal of the aqueous acrylic acid from the liquid phase below a side draw in the rectification column 4, separation of the aqueous acrylic acid above the side draw and withdrawal of the acrylic acid-rich phase (crude acrylic acid) in liquid form in the side draw.

The crude acrylic acid can be purified further by crystallization.

Oligomeric 3-hydroxypropionic acid is the product of at least two molecules of 3-hydroxypropionic acid. These molecules are bonded to one another via esterification of the carboxyl group of one molecule with the hydroxyl group of the other molecule.

Oligomeric acrylic acid is the product of at least two molecules of acrylic acid. These molecules are bonded to one another via Michael addition of the carboxyl group of one molecule with the ethylenic double bond of the other molecule.

The process according to the invention is described hereinafter:

Preparation of 3-hydroxypropionic acid

In the process according to the invention, preference is given to using aqueous 3-hydroxypropionic acid produced by fermentation. Such a process is disclosed, for example, in WO 02/090312 A1.

Preparation of acrylic acid

Some of the water can be distilled out of the aqueous 3-hydroxypropionic acid, in the course of which some of the monomeric 3-hydroxypropionic acid is converted to oligomeric 3-hydroxypropionic acid with elimination of water.

The temperature in the conversion is preferably less than 100° C., more preferably less than 90° C., most preferably less than 80° C. Excessively high temperatures in step i) promote the unwanted dehydration of monomeric 3-hydroxypropionic acid to acrylic acid.

The pressure in the conversion is preferably from 10 to 300 mbar, more preferably from 20 to 200 mbar, most preferably from 40 to 150 mbar. Relatively low pressures in step i) enable gentle removal of the water from the liquid phase. Excessively low pressures are uneconomic.

The heat can be supplied via internal and/or external heat exchangers of conventional design and/or via jacket heating (the heat transfer medium used is advantageously steam). The heat is preferably supplied via external circulation evaporators with natural or forced circulation. Particular preference is given to using external circulation evaporators with forced circulation.

Evaporators of this kind are described in EP 0 854 129 A1 . The use of a plurality of evaporators, connected in series or in parallel, is possible.

The pH during the distillation is preferably at least 1.5, more preferably at least 1.8, most preferably at least 2.0 . Excessively low pH values increase oligomer formation and shift the ratio of monomeric 3-hydroxypropionic acid to oligomeric 3-hydroxypropionic acid. An excessively high proportion of long-chain oligomers increases the viscosity and worsens the heat transfer. Thus, it is customary not to add any compounds that catalyze the oligomerization, especially no strong acids such as sulfuric acid, organic sulfonic acids and phosphoric acid.

The aqueous mixture of monomeric 3-hydroxypropionic acid and oligomeric 3-hydroxypropionic acid obtained comprises preferably from 5 to 50% by weight of water, more preferably from 10 to 40% by weight of water, most preferably from 15 to 35% by weight of water.

The aqueous mixture of monomeric 3-hydroxypropionic acid and oligomeric 3-hydroxypropionic acid obtained comprises preferably from 10% to 60% by weight of monomeric 3-hydroxypropionic acid, more preferably from 20% to 50% by weight of monomeric 3-hydroxypropionic acid, most preferably from 25% to 45% by weight of monomeric 3-hydroxypropionic acid.

The water content is lowered preferably by at least 5% by weight, more preferably by at least 10% by weight, most preferably by at least 15% by weight. The value by which the water content has been lowered is the difference between the water content of the aqueous 3-hydroxypropionic acid used (reactant) and the water content of the aqueous mixture of monomeric 3-hydroxypropionic acid and oligomeric 3-hydroxypropionic acid obtained (product).

The water content can be determined by the customary methods, for example by means of Karl Fischer titration.

The content of monomeric 3-hydroxypropionic acid is lowered preferably by at least 5% by weight, more preferably by at least 15% by weight, most preferably by at least 25% by weight. The value by which the content of monomeric 3-hydroxypropionic acid has been lowered is the difference between the content of monomeric 3-hydroxypropionic acid in the aqueous 3-hydroxypropionic acid used (reactant) and the content of monomeric 3-hydroxypropionic acid in the aqueous mixture of monomeric 3-hydroxypropionic acid and oligomeric 3-hydroxypropionic acid obtained (product).

The content of monomeric 3-hydroxypropionic acid and oligomeric 3-hydroxypropionic acid can be determined by means of HPLC. To determine the oligomeric 3-hydroxypropionic acid, the signals for the first four oligomers, i.e. up to the pentamer, are evaluated using the calibration factor for the monomeric 3-hydroxypropionic acid and the sum is formed.

Monomeric acrylic acid and oligomeric acrylic acid can be determined analogously.

The water is advantageously removed by means of a rectification column 1 . The rectification column 1 is of a design known per se and has the standard internals. The column internals used may in principle be all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids.

The feed into the rectification column 1 is appropriately effected into the lower region thereof. The feed temperature is preferably from 20 to 100° C., more preferably from 30 to 80° C., most preferably from 40 to 60° C. Particular preference is given to dual-flow trays below the feed (stripping section) and Thormann trays above the feed (rectifying section). In general, 2 to 5 theoretical plates below the feed and 2 to 15 theoretical plates above the feed of the rectification column 1 are adequate. The rectification is typically conducted in such a way that the bottom pressure required for the conversion is established. The top pressure depends on the bottom pressure, the number and type of column internals and the fluid-dynamic requirements of the rectification.

To increase the residence time and hence to enhance the conversion of monomeric 3-hydroxypropionic acid to oligomeric 3-hydroxypropionic acid, it is advantageous to convey a portion of the bottoms liquid together with the feed into the lower region of the rectification column 1 . As a result of this, some of the bottoms liquid is circulated via the trays below the feed (stripping section).

The rectification column 1 is typically manufactured from austenitic steel, preferably from material 1.4571 (to DIN EN 10020).

The water removed at the top of the rectification column 1 can be cooled indirectly, for example by means of heat exchangers which are known per se to those skilled in the art and are not subject to any particular restriction, or directly, for example by means of a quench. For this purpose, already condensed water is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point for the water advantageously takes the form of a collecting tray. Internals which improve the mixing of the cooled water with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 1. The direct condensation of the water can also be executed in more than one stage, with temperature decreasing in the upward direction. Preferably, however, the cooling is effected by indirect cooling.

The aqueous mixture of monomeric 3-hydroxypropionic acid and oligomeric 3-hydroxypropionic acid thus obtained is withdrawn continuously from the bottom of the distillation and converted to acrylic acid.

The conversion of the aqueous mixture of monomeric 3-hydroxypropionic acid and oligomeric 3-hydroxypropionic acid to acrylic acid is performed in the liquid phase at a temperature of preferably 130 to 220° C., more preferably of 150 to 200° C., most preferably of 160 to 190° C. The pressure is preferably from 25 to 750 mbar, more preferably from 50 to 500 mbar, most preferably from 100 to 300 mbar. At low pressure, the liquid phase comprises less monomeric acrylic acid, and, in the case of a distillative removal of the acrylic acid formed, the unwanted formation of oligomeric acrylic acid in the condensate is suppressed.

The heat can be supplied via internal and/or external heat exchangers of conventional design and/or via jacket heating (the heat transfer medium used is advantageously steam). The heat is preferably supplied via external circulation evaporators with natural or forced circulation. Particular preference is given to using external circulation evaporators with forced circulation. Evaporators of this kind are described in EP 0 854 129 A1. The use of a plurality of evaporators, connected in series or in parallel, is possible.

The liquid phase preferably comprises a polymerization inhibitor 1. Suitable polymerization inhibitors 1 are phenothiazine, hydroquinone and/or hydroquinone monomethyl ether. Very particular preference is given to phenothiazine and hydroquinone monomethyl ether. The liquid phase comprises preferably from 0.001 to 5% by weight, more preferably from 0.01 to 2% by weight and most preferably from 0.1 to 1% by weight of the polymerization inhibitor 1. Advantageously, an oxygen-containing gas is additionally used to inhibit polymerization. Particularly suitable for this purpose are air/nitrogen mixtures having an oxygen content of 6% by volume (lean air). If an oxygen-containing gas is used to inhibit polymerization, this is preferably supplied below the evaporator.

The liquid phase comprises preferably from 20 to 95% by weight, more preferably from 40 to 85% by weight and most preferably from 50 to 80% by weight of the high-boiling organic solvent.

The boiling point of the high-boiling organic solvent at 1013 mbar is in the range from preferably 200 to 350° C., more preferably from 250 to 320° C., most preferably from 280 to 300° C. Suitable high-boiling organic solvents are, for example, dimethyl phthalate, diethyl phthalate, dimethyl isophthalate, diethyl isophthalate, dimethyl terephthalate, diethyl terephthalate, alkanoic acids such as nonanoic acid and decanoic acid, biphenyl and/or diphenyl ether.

The conversion of the aqueous mixture of 3-hydroxypropionic acid and oligomeric 3-hydroxypropionic acid may be base- or acid-catalyzed. Suitable basic catalysts are high-boiling tertiary amines, such as pentamethyldiethylenetriamine. Suitable acidic catalysts are high-boiling inorganic or organic acids, such as phosphoric acid and dodecylbenzenesulfonic acid. "High-boiling" here means a boiling point at 1013 mbar of preferably at least 160° C., more preferably at least 180° C., most preferably at least 190° C.

If a catalyst is used, the amount of catalyst in the liquid phase is preferably from 1 to 60% by weight, more preferably from 2 to 40% by weight, most preferably from 5 to 20% by weight.

The aqueous acrylic acid formed in the conversion of the aqueous mixture of monomeric 3-hydroxypropionic acid and oligomeric 3-hydroxypropionic acid is preferably removed by distillation, more preferably by means of a rectification column (rectification column 2).

When a rectification column 2 is used, the conversion of the aqueous mixture of monomeric 3-hydroxypropionic acid and oligomeric 3-hydroxypropionic acid to acrylic acid takes place in the bottom of the rectification column 2, and the aqueous mixture of monomeric 3-hydroxypropionic acid and oligomeric 3-hydroxypropionic acid is the feed to the rectification column 2.

When a rectification column 2 is used, the polymerization inhibitor 1 is metered in at least partly via the reflux.

The rectification column 2 is of a design known per se and has the standard internals. The column internals used may in principle be all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids. Particular preference is given to dual-flow trays.

In general, from 3 to 10 theoretical plates are sufficient in the rectification column 2. The rectification is typically conducted under standard pressure. The top pressure is preferably from 50 to 900 mbar, more preferably from 200 to 600 mbar, most preferably from 300 to 400 mbar. When the top pressure is excessively high the aqueous acrylic acid is subjected to unnecessary thermal stress, and when the top pressure is excessively low the process becomes too technically complex. The bottom pressure depends on the top pressure, the number and type of column internals and the fluid-dynamic requirements of the rectification.

The rectification column 2 is typically manufactured from austenitic steel, preferably from material 1.4571 (to DIN EN 10020).

The aqueous acrylic acid removed at the top of the rectification column 2 can be cooled indirectly, for example by means of heat exchangers which are known per se to those skilled in the art and are not subject to any particular restriction, or directly, for example by means of a quench. It is preferably cooled directly. For this purpose, already condensed aqueous acrylic acid is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point for the aqueous acrylic acid advantageously takes the form of a collecting tray. Internals which improve the mixing of the cooled aqueous acrylic acid with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 2. The direct condensation of the aqueous acrylic acid can also be executed in more than one stage, with temperature decreasing in the upward direction. Preferably, the cooling is effected by direct cooling.

Some of the aqueous acrylic acid withdrawn at the top of the rectification column 2, preferably 10 to 40% by weight based on the total amount of distillate, is used as reflux for the rectification column 2; the remainder of the aqueous acrylic acid is discharged.

When a high-boiling organic solvent having low solubility in water is used, the condensed distillate of the rectification column 2 can be separated by means of a phase separator. The organic phase can be recycled into the rectification column 2, for example into the bottom of the rectification column 2. The aqueous phase can likewise be recycled partly into the rectification column 2, for example as reflux and for direct cooling of the vapor.

The bottoms residue of the rectification column 2 can be discharged and sent to a residue distillation or a residue cleavage. The bottoms residue is preferably conducted through a solids separator (cyclone) and optionally supplemented with fresh inert organic solvent 1.

The aqueous acrylic acid obtained is separated by distillation into an acrylic acid-rich phase (crude acrylic acid) and a water-rich phase (acid water).

The heat can be supplied via internal and/or external heat exchangers of conventional design and/or via jacket heating (the heat transfer medium used is advantageously steam). The heat is preferably supplied via external circulation evaporators with natural or forced circulation. Particular preference is given to using external circulation evaporators with forced circulation.

Evaporators of this kind are described in EP 0 854 129 A1. The use of a plurality of evaporators, connected in series or in parallel, is possible.

The aqueous acrylic acid preferably comprises a polymerization inhibitor 2. Suitable polymerization inhibitors 2 are phenothiazine, hydroquinone and/or hydroquinone monomethyl ether. Very particular preference is given to phenothiazine and hydroquinone monomethyl ether. The liquid phase comprises preferably from 0.001 to 5% by weight, more preferably from 0.01 to 2% by weight and most preferably from 0.1 to 1% by weight of the polymerization inhibitor 2. Advantageously, an oxygen-containing gas is additionally used to inhibit polymerization. Particularly suitable for this purpose are air/nitrogen mixtures having an oxygen content of 6% by volume (lean air). If an oxygen-containing gas is used to inhibit polymerization, this is preferably supplied below the evaporator.

Advantageously, a polymerization inhibitor 3 is added to the acrylic acid-rich phase (crude acrylic acid) removed. Suitable polymerization inhibitors 3 are phenothiazine, hydroquinone and/or hydroquinone monomethyl ether. Very particular preference is given to phenothiazine and hydroquinone monomethyl ether.

To promote the separation of the aqueous acrylic acid into an acrylic acid-rich phase (crude acrylic acid) and a water-rich phase (acid water), an entraining agent can be added. Suitable entraining agents are low-boiling hydrophobic organic solvents having a solubility in water at 23° C. preferably less than 5 g per 100 ml of water, more preferably less than 1 g per 100 ml of water, most preferably of less than 0.2 g per 100 ml of water, and a boiling point at 1013 mbar in the range from preferably 60 to 160° C., more preferably from 70 to 130° C., most preferably from 75 to 115° C. Suitable hydrophobic organic solvents are, for example, aliphatic hydrocarbons such as hexane, heptane, dodecane, cyclohexane, methylcyclohexane, isooctane and hydrogenated triisobutylene, aromatic hydrocarbons such as benzene, toluene, xylene and ethylbenzene, ketones such as methyl isobutyl ketone, ethers such as methyl tert-butyl ether, or mixtures thereof.

Distillative separation of the aqueous acrylic acid into an acrylic acid-rich phase (crude acrylic acid) and a water-rich phase (acid water) is preferably accomplished using a rectification column 3.

When a rectification column 3 is used, the polymerization inhibitor 2 is metered in at least partly via the reflux.

The rectification column 3 is of a design known per se and has the standard internals. The column internals used may in principle be all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids. Particular preference is given to dual-flow trays.

In general, from 10 to 30 theoretical plates are sufficient in the rectification column 3. The rectification is typically conducted under standard pressure. The top pressure is preferably from 50 to 600 mbar, more preferably from 150 to 400 mbar, most preferably from 200 to 300 mbar. When the top pressure is excessively high the aqueous acrylic acid is subjected to unnecessary thermal stress, and when the top pressure is excessively low the process becomes too technically complex. The bottom pressure depends on the top pressure, the number and type of column internals and the fluid-dynamic requirements of the rectification.

The rectification column 3 is typically manufactured from austenitic steel, preferably from material 1.4571 (to DIN EN 10020).

The water-rich phase (acid water) removed at the top of the rectification column 3 can be cooled indirectly, for example by means of heat exchangers which are known per se to those skilled in the art and are not subject to any particular restriction, or directly, for example by means of a quench. It is preferably cooled directly. For this purpose, already condensed water-rich phase (acid water) is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point for the water-rich phase (acid water) advantageously takes the form of a collecting tray. Internals which improve the mixing of the cooled water-rich phase (acid water) with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 3. The direct condensation of the water-rich phase (acid water) can also be executed in more than one stage, with temperature decreasing in the upward direction. Preferably, the cooling is effected by direct cooling.

Some of the water-rich phase (acid water) condensed at the top of the rectification column 3 can be used as reflux; the rest of the water-rich phase (acid water) is discharged and sent to an acid water extraction for recovery of acrylic acid.

When a hydrophobic organic solvent is used, the condensed distillate of the rectification column 3 is separated by means of a phase separator. The organic phase can be recycled into the rectification column 3, for example as reflux.

The acrylic acid-rich phase (crude acrylic acid) withdrawn from the bottom of the rectification column 3 can be used directly for production of water-absorbing polymer particles. Preference is given to further purifying the acrylic acid-rich phase (crude acrylic acid) by crystallization. The mother liquor obtained in the crystallization can be recycled into the rectification column 3, preferably below the removal point for the acrylic acid-rich phase (crude acrylic acid).

The acrylic acid-rich phase (crude acrylic acid) can be purified by layer crystallization, as described, for example, in EP 0 616 998 A1, or by suspension crystallization, as described in DE 100 39 025 A1. Suspension crystallization is preferred. The combination of a suspension crystallization with a wash column, as described in WO 2003/041832 A1, is particularly preferred.

In a particularly preferred embodiment of the present invention, the removal of the aqueous acrylic acid from the liquid phase and the separation of the aqueous acrylic acid into an acrylic acid-rich phase (crude acrylic acid) and a water-rich phase (acid water) is conducted by means of a rectification column having a side draw (rectification column 4). The rectification column 4 combines the tasks performed by the rectification columns 2 and 3 in a single rectification column. The section below the side draw corresponds here to the rectification column 2 and the section above the side draw to the rectification column 3.

When a rectification column 4 is used, the conversion of the aqueous mixture of monomeric 3-hydroxypropionic acid and oligomeric 3-hydroxypropionic acid to acrylic acid takes place in the bottom of the rectification column 4, and aqueous mixture of monomeric 3-hydroxypropionic acid and oligomeric 3-hydroxypropionic acid is the feed to the rectification column 4.

The feed into the rectification column 4 is appropriately effected in the lower region thereof. It is preferably effected below the first tray of the rectification column 4 . The feed temperature is preferably from 25 to 150° C., more preferably from 40 to 100° C., most preferably from 50 to 70° C.

The heat is supplied in the bottom of the rectification column 4 via internal and/or external heat exchangers (the heat transfer medium is again preferably steam) of conventional design and/or via jacket heating. The heat is preferably supplied via external circulation evaporators with natural or forced circulation. Particular preference is given to external circulation evaporators with forced circulation. Evaporators of this kind are described in EP 0 854 129 A1. The use of a plurality of evaporators, connected in series or in parallel, is possible. Preference is given to operating 2 to 4 evaporators in parallel.

If an oxygen-containing gas is used to inhibit polymerization, this is preferably supplied below the evaporator. The bottoms residue of the rectification column 4 can be discharged and sent to a residue distillation or a residue cleavage. The bottoms residue is preferably conducted through a solids separator (cyclone) and optionally supplemented with fresh high-boiling organic solvent.

The acrylic acid-rich phase (crude acrylic acid) is withdrawn via the side draw of the rectification column 4 . The withdrawal of the acrylic acid-rich phase (crude acrylic acid) is effected in a customary manner and is not subject to any restriction. A suitable removal method is via a collecting tray, in which case the entire reflux is collected and a portion is discharged and the other portion is used as reflux below the collecting tray, or via a tray with integrated removal means, preferably via a dual-flow tray with integrated removal means.

The acrylic acid-rich phase (crude acrylic acid) withdrawn is cooled by means of a heat exchanger (an example of a suitable coolant is surface water). The use of a plurality of heat exchangers, connected in series or in parallel, is possible. The heat exchangers are known per se to those skilled in the art and are not subject to any particular restriction.

The acrylic acid-rich phase (crude acrylic acid) withdrawn is discharged and some is used as solvent for the polymerization inhibitor 2.

The water-rich phase (acid water) removed at the top of the rectification column 4 can be cooled indirectly, for example by means of heat exchangers which are known per se to those skilled in the art and are not subject to any particular restriction, or directly, for example by means of a quench. It is preferably cooled directly. For this purpose, already condensed water-rich phase (acid water) is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point for the water-rich phase (acid water) advantageously takes the form of a collecting tray. Internals which improve the mixing of the cooled water-rich phase (acid water) with the vapor can enhance the effect of the direct cooling. All standard internals are useful in principle for this purpose, for example trays, structured packings and/or random packings. Among the trays, preference is given to bubble-cap trays, sieve trays, valve trays, Thormann trays and/or dual-flow trays. Among the random packings, preference is given to those comprising rings, helices, saddles, Raschig, Intos or Pall rings, Berl or Intalox saddles, or braids. Particular preference is given to dual-flow trays. In general, 2 to 5 theoretical plates are sufficient here. These trays are not included in the figures given so far for the number of theoretical plates in the rectification column 4 . The direct condensation of the water-rich phase (acid water) can also be executed in more than one stage, with temperature decreasing in the upward direction. Preferably, the cooling is effected by direct cooling.

Some of the water-rich phase (acid water) condensed at the top of the rectification column 4 can be used as reflux; the rest of the water-rich phase (acid water) is discharged and sent to an acid water extraction for recovery of acrylic acid.

When a hydrophobic organic solvent is used, the condensed distillate of the rectification column 4 can be separated by means of a phase separator. The organic phase can be recycled into the rectification column 4, for example as reflux.

In a preferred embodiment of the present invention, a dividing wall column is used as the rectification column 4 . A dividing wall column has a vertical dividing wall which divides the cross section of part of the column into two sections. The reflux is divided between the two column sections. The feed and the side draw of the dividing wall column are on different sides of the dividing wall.

The crude acrylic acid withdrawn from the rectification column 4 can be used directly for production of water-absorbing polymer particles. Preference is given to further purifying the crude acrylic acid by crystallization. The mother liquor obtained in the crystallization can be recycled into the rectification column 4, preferably below the removal point for the crude acrylic acid.

The crude acrylic acid can be purified by layer crystallization, as described, for example, in EP 0 616 998 A1, or by suspension crystallization, as described in DE 100 39 025 A1. Suspension crystallization is preferred. The combination of a suspension crystallization with a wash column, as described in WO 2003/041832 A1, is particularly preferred.

The acrylic acid thus prepared can be used directly as a monomer for preparation of homo- or copolymers, especially acrylic acid homopolymers, acrylic acid/maleic anhydride copolymers, acrylic acid/maleic acid copolymers and acrylic acid/methacrylic acid copolymers, but also for preparation of water-absorbing polymer particles and acrylic esters, e.g. methyl acrylate, ethyl acrylate, n-butyl acrylate and 2-ethylhexyl acrylate.

Production of water-absorbing polymer particles

Water-absorbing polymer particles are produced by polymerizing a monomer solution or suspension comprising
a) at least one ethylenically unsaturated monomer which bears acid groups and may be at least partly neutralized, especially partly neutralized acrylic acid,
b) at least one crosslinker,
c) at least one initiator,
d) optionally one or more ethylenically unsaturated monomers copolymerizable with the monomers mentioned under a) and
e) optionally one or more water-soluble polymers, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Further suitable monomers a) are, for example, ethylenically unsaturated sulfonic acids, such as styrenesulfonic acid and 2-acrylamido-2-methylpropanesulfonic acid (AMPS).

The proportion of acrylic acid and/or salts thereof in the total amount of monomers a) is preferably at least 50 mol %, more preferably at least 90 mol %, most preferably at least 95 mol %.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.2 to 0.5% by weight, based in each case on monomer a). With rising crosslinker content, the centrifuge retention capacity (CRC) falls and the absorption under a pressure of 21.0 $g/cm^2$ passes through a maximum.

The initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Bruggolite® FF7 (Bruggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the polymerization inhibitors typically used in acrylic acid require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. It is possible here to combine the process steps of polymerization and drying, as described in WO 2008/040715 A2, WO 2008/052971 A1 and WO 2011/026876 A1.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles having a particle size of greater than 150 μm is preferably at least 90% by weight, more preferably at least 95% by weight and most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization.

If the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles of excessively large particle size lower the free swell rate. The proportion of excessively large polymer particles should therefore likewise be low.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 5% by weight, more preferably 0.02 to 2% by weight and most preferably 0.05 to 1% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1% by weight, preferably 0.005 to 0.5% by weight and more preferably 0.02 to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The drying can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

In a preferred embodiment of the present invention, the water-absorbing polymer particles are cooled after the thermal drying. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight, based in each case on the water-absorbing polymer particles. The remoisturizing increases the mechanical stability of the polymer particles and reduces their tendency to static charging. The remoisturizing is advantageously performed in the cooler after the thermal drying.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

Methods
Determination of the 3-hydroxypropionic Acid and Acrylic Acid Contents

The 3-hydroxypropionic acid and acrylic acid contents are determined by reverse phase chromatography with ultraviolet detection.

The sample is prepared by weighing about 100 to 300 mg of sample into a 50 ml standard flask and making it up to the mark with eluent A. Eluent A is a mixture of 1000 ml of water and 1 ml of 0.5 molar sulfuric acid.

For calibration of 3-hydroxypropionic acid, four weights (about 280 mg, 180 mg, 90 mg and 60 mg) are used, with acidification (possibly re-acidification) to a pH of 3 to 4 with about 100 µl of 25% by weight sulfuric acid before making up to the mark of the 50 ml standard flask. The calibration range is 0.1 to 280 mg/50 ml.

For calibration of acrylic acid, at least two weights are diluted to at least six concentrations. The calibration range is 0.01 to 0.9 mg/50 ml.

For reverse phase chromatography, a separating column of the Prontosil 120-3-C18 AQ 3 µm, 150×4.6 mm (BISCHOFF Analysentechnik und -geräte GmbH, Leonberg, Germany) type is used. The temperature is 25° C., the injection volume is 50 µl, the flow rate is 1.5 ml/min and the run time is 15 minutes. The UV detector is set to 205 nm. From the start to 8 minutes 100% by weight of eluent A is used, from 8 to 11.5 minutes a mixture of 40% by weight of eluent A and 60% by weight of eluent B, and from 11.5 minutes to the end 100% by weight of eluent A. Eluent B is acetonitrile.

Determination of the Oligomeric 3-hydroxypropionic Acid and Oligomeric Acrylic Acid Contents The oligomeric 3-hydroxypropionic acid and oligomeric acrylic acid contents are determined by ion exclusion chromatography with refractive index detection.

To prepare the samples, the components to be analyzed are separated from the sample matrix by means of a solid phase extraction. For this purpose, an SPE cartridge of the Bakerband SiOH 6 ml, 1000 mg (J. T. Baker, Avantor Performance Materials, Inc., Center Valley, Pa., USA) type is used. The SPE cartridge is activated with 6 ml of methanol and flushed twice with 6 ml each time of eluent. The SPE cartridge must never run dry. Subsequently, the sample is pipetted onto the SPE cartridge and flushed 10 times with 1 ml of eluent each time into a 10 ml standard flask. The amount of sample used is 65 µl in the case of bottoms samples, 85 µl in the case of tops samples and 75 µl in the case of extract samples. Unless the samples comprise hydrophobic solvent (high-boiling organic solvent, entraining agent), these samples can be applied without extraction; for this purpose, 85 µl are dissolved directly in 10 ml of eluent. The eluent used is 0.1% by volume aqueous phosphoric acid.

For ion exclusion chromatography, two separating columns of the Shodex RSpak KC-811, 300×8 mm (SHOWA DENKO K.K. Shodex (Separation & HPLC) Group, Kawasaki, Japan) type are used connected in series. The temperature is 40° C., the injection volume is 100 µl, the flow rate is 1.0 ml/min and the run time is 45 minutes. The eluent used is 0.1% by weight aqueous phosphoric acid. The autosampler is cooled to 15° C.

For evaluation, the integration is preceded by a blank value subtraction. For this purpose, eluent is injected and the chromatogram thus obtained is subtracted from the sample chromatogram. The evaluation is effected in terms of area percent, with conversion to percent by weight by means of the following formula:

$$\text{Weight \% (oligomer)} = \frac{\text{Weight \% (Monomer)}}{\text{Area \% (Monomer)}} \times \text{Area \% (oligomer)}$$

To evaluate the oligomers, the contents of the dimers, trimers, tetramers and pentamers (i.e. n =2 to 5) are added up in each case. The retention times are monitored by injecting 3-hydroxypropionic acid and diacrylic acid.

Determining the pH

To determine the pH, 1.0 g of sample is dissolved or suspended in 10 ml of demineralized water at 25° C. After 10 minutes, the pH of the aqueous phase is measured at 25° C. by means of a pH electrode.

EXAMPLES

Example 1

A 2 l jacketed three-neck flask with distillation attachment was charged with 1500 g of an about 30% by weight aqueous 3-hydroxypropionic acid, water was distilled off at 100 mbar for three hours and the remaining residue was distilled at 40 mbar. The jacket was heated by means of heat transfer oil. During the distillation, the pH was in the range from 2 to 3 . The composition of distillate and distillation residue was analyzed.

TABLE 1

Composition of the distillate

| Time [h] | 3HPA [% by wt.] | AA [% by wt.] | Oligo-3HPA [% by wt.] | Oligo-AA [% by wt.] |
|---|---|---|---|---|
| 2.9 | 36.5 | 9.3 | 2.1 | 0.0 |
| 5.5 | 38.2 | 19.4 | 6.3 | 1.6 |
| 6.7 | 12.1 | 51.5 | 6.0 | 20.2 |
| 7.6 | 2.2 | 62.1 | 5.8 | 26.8 |
| 8.8 | 0.5 | 57.6 | 0.2 | 41.4 |

TABLE 2

Composition of the distillation residue

| Time [h] | Temperature [° C.] | 3HPA [% by wt.] | AA [% by wt.] | Oligo-3HPA [% by wt.] | Oligo-AA [% by wt.] |
|---|---|---|---|---|---|
| 2.9 | 154 | 42.3 | 0.2 | 41.5 | 9.3 |
| 5.5 | 180 | 16.3 | 0.2 | 55.9 | 21.5 |
| 6.7 | 221 | 1.7 | 0.3 | 56.9 | 37.7 |
| 7.6 | 224 | 0.3 | 0.3 | 38.0 | 59.7 |
| 8.8 | 230 | 0.1 | 0.4 | 31.2 | 58.1 |

3HPA 3-hydroxypropionic acid
AA acrylic acid
Oligo-3HPA oligomeric 3-hydroxypropionic acid
Oligo-AA oligomeric acrylic acid The results show that, in the distillation residue, monomeric 3-hydroxypropionic acid is first converted to oligomeric 3-hydroxypropionic acid. Only thereafter is there significant formation of acrylic acid and oligomeric acrylic acid. The dehydration of 3-hydroxypropionic acid probably proceeds via oligomeric 3-hydroxypropionic acid as an intermediate. For a high yield and a high selectivity, monomeric 3-hydroxypropionic acid therefore has to be converted to oligomeric 3-hydroxypropionic acid.

Example 2

The conversion of monomeric 3-hydroxypropionic acid to oligomeric 3-hydroxypropionic acid is performed in a reactor with a forced circulation flash evaporator and attached rectification column 1.

The reactor used is a jacketed 3 l glass vessel. The amount of liquid in the reactor is about 2500 g. The reactor is simultaneously the bottom of the rectification column 1.

The forced circulation flash evaporator consists of a pump, a heat exchanger and a pressure-retaining valve. The reactor contents are circulated through the heat exchanger and the pressure-retaining valve by means of a pump.

The rectification column 1 used is a 10-tray bubble-cap tray column having an internal diameter of 50 mm. The rectification column 1 is electrically trace-heated.

As feed, 1000 g/h of aqueous 3-hydroxypropionic acid are conveyed to the 5th tray of the bubble-cap tray column. The aqueous 3-hydroxypropionic acid has the following composition:
40.2% by weight of water,
2.1% by weight of acrylic acid,
0.1% by weight of oligomeric acrylic acid,
52.6% by weight of 3-hydroxypropionic acid and
5.0% by weight of oligomeric 3-hydroxypropionic acid.

The forced circulation flash evaporator is used to circulate the reactor contents. Upstream of the pressure-retaining valve, the pressure is 2.0 bar and the temperature is 175° C.

The pressure at the top of the rectification column 1 is 100 mbar. The vapor is condensed by means of a condenser and partly recycled as reflux into the rectification column 1 and partly discharged. 298.8 g/h of condensate are discharged. The condensate has the following composition:
99.1% by weight of water,
0.9% by weight of acrylic acid and
<0.0001% by weight of 3-hydroxypropionic acid.

701.2 g/h of an aqueous mixture of monomeric 3-hydroxypropionic acid and oligomeric 3-hydroxypropionic acid are discharged from the reactor. The mixture has the following composition:
20.1% by weight of water,
0.2% by weight of acrylic acid,
2.5% by weight of oligomeric acrylic acid,
32.4% by weight of 3-hydroxypropionic acid and
44.8% by weight of oligomeric 3-hydroxypropionic acid.

Example 3

The conversion of monomeric 3-hydroxypropionic acid to oligomeric 3-hydroxypropionic acid is performed in a reactor with a forced circulation flash evaporator and attached rectification column 1.

The reactor used is a jacketed 3 l glass vessel. The amount of liquid in the reactor is about 2500 g. The reactor is simultaneously the bottom of the rectification column 1.

The forced circulation flash evaporator consists of a pump, a heat exchanger and a pressure-retaining valve. The reactor contents are circulated through the heat exchanger and the pressure-retaining valve by means of the pump.

The rectification column 1 used is a 10-tray bubble-cap tray column having an internal diameter of 50 mm. The rectification column 1 is electrically trace-heated.

As feed, 1000 g/h of aqueous 3-hydroxypropionic acid are conveyed to the 5th tray of the bubble-cap tray column. The aqueous 3-hydroxypropionic acid has the following composition:
40.2% by weight of water,
2.1% by weight of acrylic acid,
0.1% by weight of oligomeric acrylic acid,
52.6% by weight of 3-hydroxypropionic acid and
5.0% by weight of oligomeric 3-hydroxypropionic acid.

The forced circulation flash evaporator is used to circulate the reactor contents. Upstream of the pressure-retaining valve, the pressure is 2.0 bar and the temperature is 175° C.

500 g/h of the reactor contents are withdrawn, mixed with the feed and conveyed to the 5th tray of the bubble-cap tray column.

The pressure at the top of the rectification column 1 is 100 mbar. The vapor is condensed by means of a condenser and partly recycled as reflux into the rectification column 1 and partly discharged. 314.9 g/h of condensate are discharged. The condensate has the following composition:
99.35% by weight of water,
0.65% by weight of acrylic acid and
<0.0001% by weight of 3-hydroxypropionic acid.

685.1 g/h of an aqueous mixture of monomeric 3-hydroxypropionic acid and oligomeric 3-hydroxypropionic acid are discharged from the reactor. The mixture has the following composition:
18.7% by weight of water,
<0.05% by weight of acrylic acid,
2.9% by weight of oligomeric acrylic acid, 28.4% by weight of 3-hydroxypropionic acid and
50.0% by weight of oligomeric 3-hydroxypropionic acid.

Example 4

The conversion of an aqueous mixture of monomeric 3-hydroxypropionic acid and oligomeric 3-hydroxypropionic acid to acrylic acid is performed in a reactor with a forced circulation flash evaporator and attached rectification column 4.

The reactor used is a jacketed 5 l glass vessel. The amount of liquid in the reactor is about 4000 g. The temperature in the reactor is 174° C. The pressure in the reactor is 360 mbar. The reactor is simultaneously the bottom of the rectification column 4.

The forced circulation flash evaporator consists of a pump, a heat exchanger and a pressure-retaining valve. The reactor contents are circulated through the heat exchanger and the pressure-retaining valve by means of the pump. The feed of aqueous mixture of monomeric 3-hydroxypropionic acid and oligomeric 3-hydroxypropionic acid and of high-boiling solvent is metered into the circuit upstream of the heat exchanger. Below the heat exchanger, 9 l/h of an air/nitrogen mixture having an oxygen content of 6% by volume (lean air) are metered into the circuit.

250 g/h of aqueous mixture of monomeric 3-hydroxypropionic acid and oligomeric 3-hydroxypropionic acid and 35 g/h of high-boiling solvent are used as feed. The aqueous mixture of monomeric 3-hydroxypropionic acid and oligomeric 3-hydroxypropionic acid has the following composition:
  29.5% by weight of water,
  0.7% by weight of acrylic acid,
  0.1% by weight of oligomeric acrylic acid,
  39.8% by weight of 3-hydroxypropionic acid,
  27.3% by weight of oligomeric 3-hydroxypropionic acid,
  0.9% by weight of 2-hydroxypropionic acid,
  0.4% by weight of succinic acid,
  0.015% by weight of formaldehyde,
  0.001% by weight of acetaldehyde,
  0.012% by weight of arabitol,
  0.041% by weight of erythritol,
  0.7% by weight of 2-hydroxy(iso)valeric acid,
  glucose, glucose esters and further high boilers.

The high-boiling solvent used was diethyl phthalate. The high-boiling solvent additionally comprised 0.1% by weight of phenothiazine and 0.5% by weight of hydroquinone monomethyl ether.

54 g/h of residue are withdrawn from the reactor.

The rectification column 4 has an internal diameter of 50 mm and is electrically trace-heated. The rectification column as a total of 80 trays and a side draw, with 20 dual-flow trays below the side draw and 60 bubble-cap trays above the side draw.

The side draw between the 20th and 21st trays is a collecting tray. The liquid is withdrawn completely therefrom as crude acrylic acid and conveyed by means of a pump through a heat exchanger, in the course of which it is cooled to 15° C., and transferred into a suspension crystallizer. 294 g/h of crude acrylic acid having the following composition are obtained:
  3.0% by weight of water,
  97.0% by weight of acrylic acid,
  <0.001% by weight of 3-hydroxypropionic acid,
  <0.001% by weight of diethyl phthalate,
  0.020% by weight of phenothiazine,
  0.040% by weight of hydroquinone monomethyl ether,
  <0.001% by weight of ethanol,
  0.006% by weight of ethyl acrylate,
  <0.001% by weight of 2-hydroxypropionic acid,
  <0.001% by weight of formaldehyde,
  <0.001% by weight of acetaldehyde and
  <0.001% by weight of 2-hydroxy(iso)valeric acid.

For suspension crystallization, a 3 l glass vessel with helical stirrer is used. The heat of crystallization is removed by means of a cooled jacket. The temperature of the crystal suspension in the glass vessel is 7.9° C. The crystal suspension obtained in the crystallization is separated discontinuously into crystals and mother liquor by means of a centrifuge at 2000 rpm with a spin time of 1 min. The crystals are washed with glacial acrylic acid and melted. The mother liquor is heated to 70° C. and metered completely to the 10th tray of the rectification column 4.

Two 5 l jacketed glass vessels are used as a buffer between the continuous rectification and the discontinuous suspension crystallization.

10 g/h of a 0.5% by weight solution of phenothiazine in crude acrylic acid are metered to the 45th tray of the rectification column 4, and 5 g/h of a 1.0% by weight solution of hydroquinone monomethyl ether in acid water are metered to the 80th tray of the rectification column 4.

The vapor obtained at the top of the rectification column 4 is cooled to 20° C. and condensed in a heat exchanger (acid water). 7000 g/h of the acid water are sprayed in the vapor upstream of the heat exchanger, 184 g/h are metered to the 80th tray of the rectification column 4, and 83 g/h are discharged. The acid water has the following composition:
  95.0% by weight of water,
  5.0% by weight of acrylic acid,
  0.025% by weight of ethanol,
  0.015% by weight of ethyl acrylate,
  <0.001% by weight of formaldehyde and
  <0.001% by weight of acetaldehyde.

The offgas is conducted through a further heat exchanger (post-condenser).

Example 5

The conversion of an aqueous mixture of monomeric 3-hydroxypropionic acid and oligomeric 3-hydroxypropionic acid to acrylic acid is performed in a reactor with a forced circulation flash evaporator and attached rectification column 4. At the top of the rectification column, an entraining agent is added.

The reactor used is a jacketed 5 l glass vessel. The amount of liquid in the reactor is about 4000 g. The temperature in the reactor is 167° C. The pressure in the reactor is 230 mbar. The reactor is simultaneously the bottom of the rectification column 4.

The forced circulation flash evaporator consists of a pump, a heat exchanger and a pressure-retaining valve. The reactor contents are circulated through the heat exchanger and the pressure-retaining valve by means of the pump. The feed of aqueous mixture of monomeric 3-hydroxypropionic acid and oligomeric 3-hydroxypropionic acid and of high-boiling solvent is metered into the circuit upstream of the heat exchanger. Below the heat exchanger, 13 l/h of an air/nitrogen mixture having an oxygen content of 6% by volume (lean air) are metered into the circuit.

250 g/h of aqueous mixture of monomeric 3-hydroxypropionic acid and oligomeric 3-hydroxypropionic acid and 35 g/h of high-boiling solvent are used as feed. The aqueous mixture of monomeric 3-hydroxypropionic acid and oligomeric 3-hydroxypropionic acid has the following composition:
- 29.5% by weight of water,
- 0.7% by weight of acrylic acid,
- 0.1% by weight of oligomeric acrylic acid,
- 39.8% by weight of 3-hydroxypropionic acid,
- 27.3% by weight of oligomeric 3-hydroxypropionic acid,
- 0.9% by weight of 2-hydroxypropionic acid,
- 0.4% by weight of succinic acid,
- 0.015% by weight of formaldehyde,
- 0.001% by weight of acetaldehyde,
- 0.012% by weight of arabitol,
- 0.041% by weight of erythritol,
- 0.7% by weight of 2-hydroxy(iso)valeric acid,
- glucose, glucose esters and further high boilers.

The high-boiling solvent used was diethyl phthalate. The high-boiling solvent additionally comprised 0.1% by weight of phenothiazine and 0.5% by weight of hydroquinone monomethyl ether.

53 g/h of residue are withdrawn from the reactor.

The rectification column 4 has an internal diameter of 50 mm and is electrically trace-heated. The rectification column has a total of 60 trays and a side draw, with 20 dual-flow trays below the side draw and 40 bubble-cap trays above the side draw.

The side draw between the 20th and 21st trays is a collecting tray. The liquid is withdrawn completely therefrom as crude acrylic acid and conveyed by means of a pump through a heat exchanger, in the course of which it is cooled to 15° C., and transferred into a suspension crystallizer. 304 g/h of crude acrylic acid having the following composition are obtained:
- 3.7% by weight of water,
- 96.3% by weight of acrylic acid,
- <0.001% by weight of 3-hydroxypropionic acid,
- <0.001% by weight of diethyl phthalate,
- 0.020% by weight of phenothiazine,
- 0.040% by weight of hydroquinone monomethyl ether,
- <0.001% by weight of ethanol,
- <0.001% by weight of ethyl acrylate,
- <0.001% by weight of 2-hydroxypropionic acid,
- <0.001% by weight of formaldehyde,
- <0.001% by weight of acetaldehyde,
- <0.001% by weight of 2-hydroxy(iso)valeric acid and
- <0.001% by weight of toluene.

For suspension crystallization, a 3 l glass vessel with helical stirrer is used. The heat of crystallization is removed by means of a cooled jacket. The temperature of the crystal suspension in the glass vessel is 7.9° C. The crystal suspension obtained in the crystallization is separated discontinuously into crystals and mother liquor by means of a centrifuge at 2000 rpm with a spin time of 1 min. The crystals are washed with glacial acrylic acid and melted. The mother liquor is heated to 70° C. and metered completely to the 10th tray of the rectification column 4.

Two 5 l jacketed glass vessels are used as a buffer between the continuous rectification and the discontinuous suspension crystallization.

10 g/h of a 0.5% by weight solution of phenothiazine in crude acrylic acid are metered to the 45th tray of the rectification column 4, and 5 g/h of a 1.0% by weight solution of hydroquinone monomethyl ether in acid water are metered to the 80th tray of the rectification column 4.

The vapor obtained at the top of the rectification column 4 is cooled to 20° C., condensed and collected in a phase separator. The entraining agent used is toluene. 5 g/h of toluene are metered into the organic phase in order to compensate for losses of entraining agent.

7000 g/h of the organic phase are sprayed in the vapor upstream of the heat exchanger and 465 g/h are metered to the 30th tray of the rectification column 4 . The aqueous phase (acid water) is discharged. The acid water has the following composition:
- 99.9% by weight of water,
- 0.022% by weight of acrylic acid,
- 0.014% by weight of ethanol,
- 0.0030% by weight of ethyl acrylate,
- 0.0013% by weight of formaldehyde,
- <0.001% by weight of acetaldehyde and
- 0.068% by weight of toluene.

The offgas is conducted through a further heat exchanger (post-condenser).

The invention claimed is:

1. A process for continuously dehydrating aqueous 3-hydroxypropionic acid to acrylic acid, which comprises, in a first step i), converting an aqueous mixture of 3-hydroxypropionic acid and oligomeric 3-hydroxypropionic acid to acrylic acid in the liquid phase and at a pressure of less than 900 mbar and separating aqueous acrylic acid from the liquid phase by distillation and, in a second step ii), separating the aqueous acrylic acid obtained in step i) at a pressure of less than 900 mbar, by distillation into a crude acrylic acid phase and a water phase.

2. The process according to claim 1, wherein the aqueous mixture of 3-hydroxypropionic acid and oligomeric 3-hydroxypropionic acid used in step i) comprises from 15 to 35% by weight of water.

3. The process according to claim 1, wherein the aqueous mixture of 3-hydroxypropionic acid and oligomeric 3-hydroxypropionic acid used in step i) comprises from 25 to 45% by weight of monomeric 3-hydroxypropionic acid.

4. The process according to claim 1, wherein the liquid phase in step i) comprises an organic solvent having a boiling point at 1013 mbar of at least 160° C.

5. The process according to claim 1, wherein the aqueous acrylic acid is removed in step i) by means of a rectification column.

6. The process according to claim 1, wherein an entraining agent is used in step ii).

7. The process according to claim 1, wherein the aqueous acrylic acid is separated in step ii), by means of a rectification column, into a crude acrylic acid phase and a water phase.

8. The process according to claim 1, wherein the removal of the aqueous acrylic acid from the liquid phase in step i) and/or separation of the aqueous acrylic acid into a crude acrylic acid phase and a water phase in step ii) is performed in a single rectification column, with removal of the aqueous acrylic acid from the liquid phase below a side draw in the single rectification column, separation of the aqueous acrylic acid into a crude acrylic acid phase and a water phase above the side draw and withdrawal of the crude acrylic acid phase in liquid form in the side draw.

9. The process according to claim 8, wherein the single rectification column is a dividing wall column, with the feed to the single rectification column and the side draw from the single rectification column on different sides of the dividing wall.

10. The process according to claim 1, wherein the crude acrylic acid phase obtained in step ii) is purified by crystallization.

11. The process according to claim 10, wherein the mother liquor from the crystallization is recycled into the single rectification column below the side draw.

12. The process according to claim 4, wherein the organic solvent has a boiling pint at 1013 mbar of 200 to 350° C.

* * * * *